(12) United States Patent
Gorschboth et al.

(10) Patent No.: US 8,770,757 B2
(45) Date of Patent: *Jul. 8, 2014

(54) FAST WAVE FRONT MEASUREMENT

(71) Applicant: Wavelight Laser Technologies AG, Erlangen (DE)

(72) Inventors: Claudia Gorschboth, Nuremberg (DE); Christof Donitzky, Eckental (DE)

(73) Assignee: Wavelight Laser Technologie AG, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,465

(22) Filed: May 31, 2013

(65) Prior Publication Data

US 2013/0258288 A1 Oct. 3, 2013

Related U.S. Application Data

(63) Continuation of application No. 13/457,075, filed on Apr. 26, 2012, now Pat. No. 8,454,164, which is a continuation of application No. 11/574,480, filed as application No. PCT/EP2005/009354 on Aug. 30, 2005, now Pat. No. 8,182,090.

(30) Foreign Application Priority Data

Sep. 1, 2004 (EP) ..................................... 04020783

(51) Int. Cl.
*A61B 3/10* (2006.01)
*A61B 3/14* (2006.01)

(52) U.S. Cl.
USPC ............................. 351/221; 351/205; 351/210

(58) Field of Classification Search
USPC .......................... 351/221, 200, 205, 210, 246
See application file for complete search history.

(56) References Cited

U.S. PATENT DOCUMENTS

| | | |
|---|---|---|
| 6,199,986 B1 | 3/2001 | Williams et al. |
| 6,338,559 B1 | 1/2002 | Williams et al. |
| 8,226,236 B2 | 7/2012 | Williams et al. |
| 2003/0053026 A1 | 3/2003 | Roorda |
| 2003/0071969 A1 | 4/2003 | Levine et al. |
| 2005/0041206 A1 | 2/2005 | Vogelsang et al. |
| 2006/0058682 A1 | 3/2006 | Miller et al. |

FOREIGN PATENT DOCUMENTS

DE 10154194 5/2003

OTHER PUBLICATIONS

Hofer, H., et al., "Dynamics of the Eye's Wave Aberration" Journal of the Optical Society of America, Optical Society of America, Washington, US, vol. 18, No. 3, Mar. 2001.

*Primary Examiner* — Dawayne A Pinkney
(74) *Attorney, Agent, or Firm* — Haynes and Boone, LLP

(57) ABSTRACT

Devices, systems, and methods for measuring wave fronts generated by a lens for an eye are provided. In some embodiments, a device for measuring wave fronts generated by a lens for an eye includes a radiation source for emitting test radiation to be directed at the lens and a sensor device for detecting wave fronts of incident test radiation after interaction with the lens, wherein the sensor device scans the test radiation after interaction with the lens at a scanning frequency which is at least equal in size to the frequency at which changes in wave fronts occur in the test radiation after interaction with the lens.

15 Claims, 3 Drawing Sheets

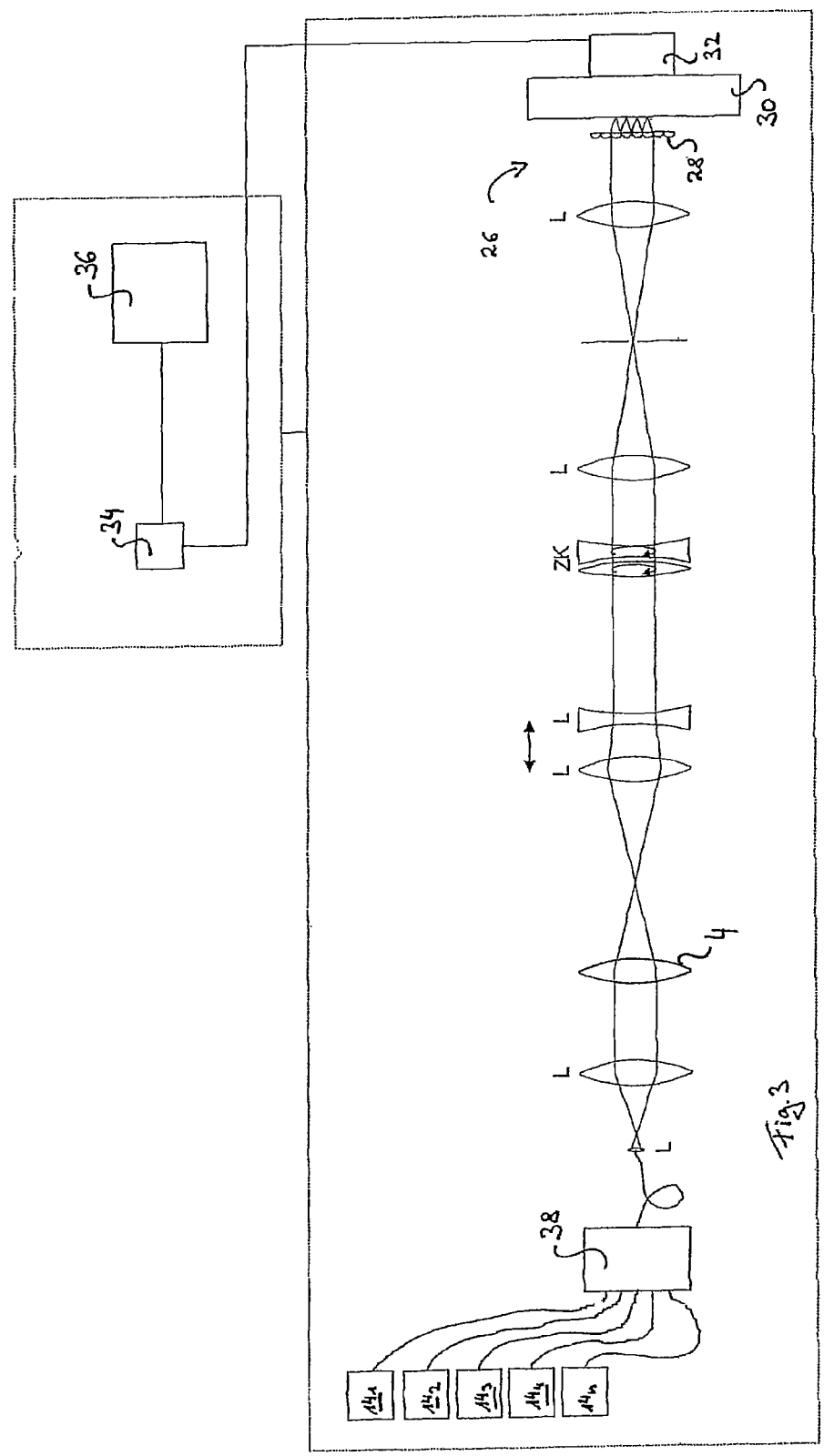

FAST WAVE FRONT MEASUREMENT

CROSS-REFERENCE TO RELATED APPLICATIONS

The present application is a continuation of U.S. Pat. No. 8,454,164, filed Apr. 26, 2012, which is a continuation of U.S. Pat. No. 8,182,090, filed Sep. 24, 2008, which is a 371 application of PCT/EP2005/009354, filed on 30 Aug. 2005, which claims priority from European Patent Application No. 04020783.9, filed 1 Sep. 2004, each of which is hereby incorporated by reference in its entirety.

TECHNICAL FIELD

The present invention relates in general to the detection of wave fronts to determine the aberration of an eye and, in particular, fast, dynamic detection of wave fronts, in order to determine non-linear imaging properties of a lens for an eye.

BACKGROUND

In ophthalmology, systems for measuring the wave front aberration of an eye are known. In practice so-called Hartmann Shack sensors have become established for wave front measurement. With these sensors the wave front to be measured is imaged by a microlens array on to a light-sensitive detector as a dot pattern. If there are deviations of the detected wave front from an ideal wave front, owing to the aberration of the eye, this can be calculated from the detected dot pattern. A narrow light beam is directed on to the eye to be examined for this purpose and light is imaged on to the Hartmann Shack sensor after interaction with the eye.

Systems for measuring wave front aberrations are used in particular in the area of refractive surgery. It is known in this case to use systems which measure the aberration of an eye when the eye fixes on a stimulus appearing at an appointed distance. More recent systems allow calculation of the aberration of an eye by detecting aberrations during fixing on a stimulus which is observed at different distances. Calculation of the aberration is done on the basis of the aberrations detected for different stimuli.

SUMMARY

The object of the present invention is to provide solutions which enable improved and more comprehensive measurement of wave fronts in general to determine the aberration of an eye and in particular to determine optical properties of lenses for an eye.

To achieve the object, the present invention provides a method, a device and uses according to the independent claims. Advantageous further developments of solutions according to the invention are defined in the dependent claims.

According to claim 1 the present invention provides a device for measuring wave fronts of a lens for an eye. A lens for an eye may in this case be understood in particular as the lens of an eye, a contact lens or an intra-ocular lens.

The device comprises a radiation source for emitting test radiation, which is to be directed at the lens. There is further a sensor device to detect wave fronts in test radiation reaching the sensor device and resulting from the test radiation of the radiation source after interaction with the lens.

The sensor device is in particular designed in such a way that it scans the incident test radiation for wave fronts at a scanning frequency which is at least equal in size to the frequency at which changes in wave fronts occur in the incident test radiation.

In this way it is achieved, for example, that even in dynamic visual situations the aberration of an eye can be correctly defined. Furthermore, in this way accommodation processes of an eye can be analysed to an extent not previously known. Furthermore, as explained below in greater detail, this enables the chromatic aberration of a lens for an eye to be defined.

The radiation source may be designed in such a way that it emits a test radiation, the wavelength of which changes at a radiation emission frequency. This means, in particular, that the wavelength of the test radiation emitted by the radiation source changes after a preset period of time. The scanning frequency of the sensor device is in this case preferably at least equal in size to the radiation emission frequency.

The device may further comprise a stimulus-generating device for generating a stimulus which is designed to effect dynamic changes of the lens. Examples of dynamic changes comprise changes of the lens owing to accommodations. The scanning frequency is in this case preferably at least equal in size to the frequency of the changes to be effected. A scanning frequency may, for example, be chosen, which is at least equal in size to the frequency at which the stimulus is varied.

The sensor device preferably comprises an optical sensor, which may be, for example, a CMOS sensor.

The sensor device may have a scanning frequency of at least 70 Hertz, 100 Hertz or more.

The sensor device may have an amplifying device to amplify test radiation incident on the sensor device, i.e. test radiation from the radiation source after interaction with the lens. The amplifying device may comprise an image amplifier, for example.

The amplifying device is preferably arranged in such a way that the amplification of the incident test radiation takes place before it is detected at the scanning frequency.

The sensor device may comprise a lens arrangement, which is configured, for example, as a function of a desired resolution and/or a desired dynamic of the sensor device in general.

The radiation source is preferably designed in such a way that its test radiation has a preset maximum radiant power, which is preset for the lens. In particular when the lens is the lens of an eye, this embodiment avoids undesired influences caused by the test radiation.

The radiation source may comprise at least one source for laser radiation, which preferably emits a fixed preset wavelength. The at least one laser beam source may, for example, be a laser, a laser diode or a superluminescent diode (SLD).

The radiation source may be connected on the output side to a switching device which can be operated at a switching frequency. This embodiment is preferred in particular if more than one laser beam source is used to direct laser radiation from the different laser beam sources on to the lens according to the switching frequency of the switching device. If only one laser beam source is used, its laser radiation may be directed at the lens according to the switching frequency, for example at predetermined times or at predetermined, regular or irregular time intervals.

The switching device preferably comprises a fibre coupler. According to one embodiment the radiation source is equipped to generate test radiation with one, two or more wavelengths in a range of between 400 nm and 1000 nm. This means it is possible, for example, to carry out fast wave front measurements with various, discrete wavelengths, which reach across the entire visible range and into the infrared range.

A Badal optometer is preferably provided as stimulus-generating device.

Furthermore, the present invention provides a method for measuring wave fronts of a lens for an eye, comprising the steps of directing a test beam on to the lens and detecting wave fronts of test radiation after interaction with the lens, detection of the test radiation taking place after interaction with the lens at a scanning frequency which is at least equal in size to the frequency at which changes in wave fronts occur in the detected test radiation.

Furthermore, the present invention provides uses of the above-described device in one of its embodiments, for measuring dynamic accommodation changes to the lens of an eye, chromatic aberrations of an eye or the dispersion of a contact lens or an intra-ocular lens for an eye or optical variations of the tear film.

BRIEF DESCRIPTION OF THE DRAWINGS

In the following description reference is made to the attached drawings.

FIG. 3 shows a schematic illustration of a preferred embodiment for detecting wave fronts of a contact lens or an intra-ocular lens for an eye.

DETAILED DESCRIPTION

Figure 1:
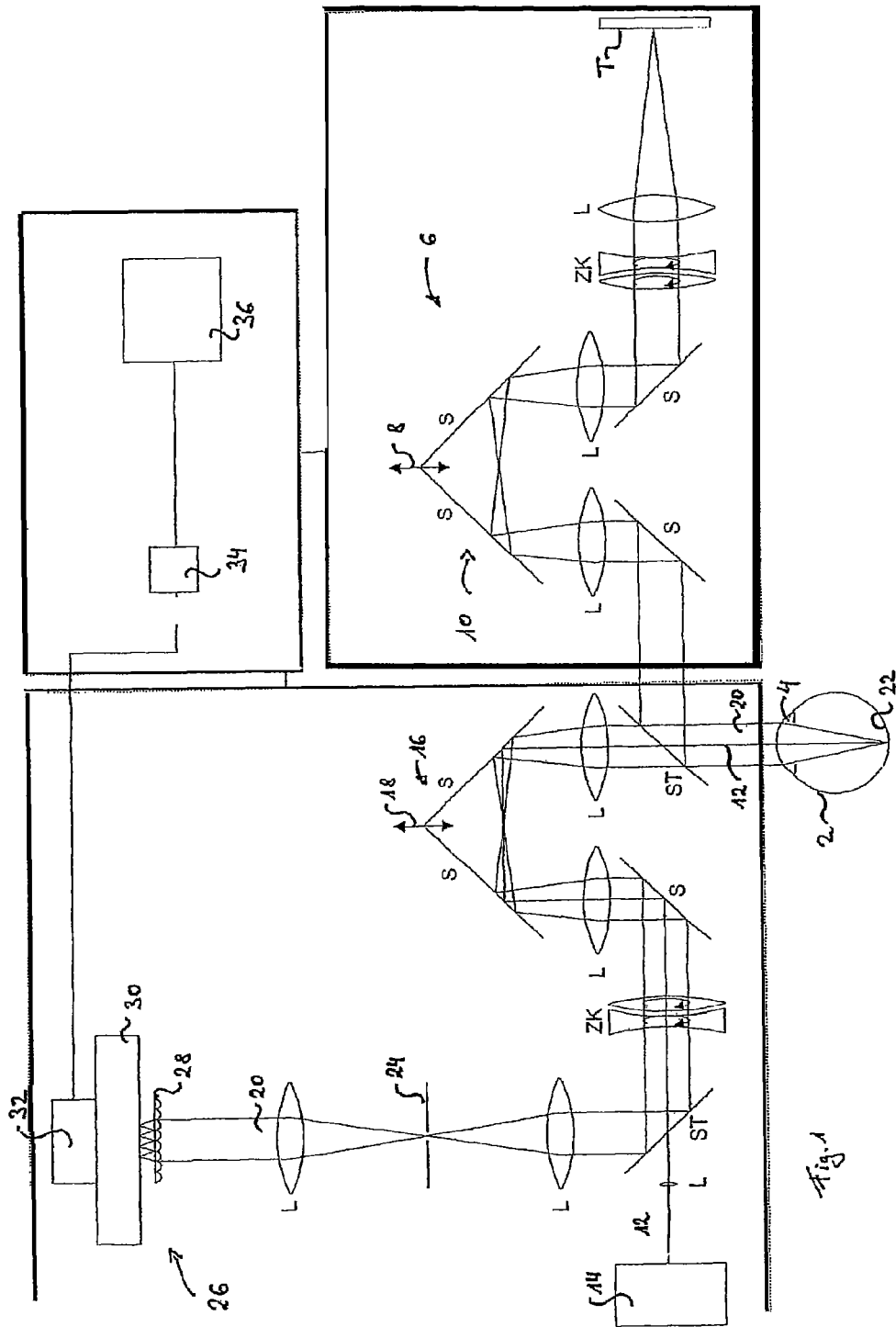
FIG. 1 shows a schematic illustration of a preferred embodiment of the device according to the invention for measuring wave fronts under dynamic visual conditions.
Figure 2:
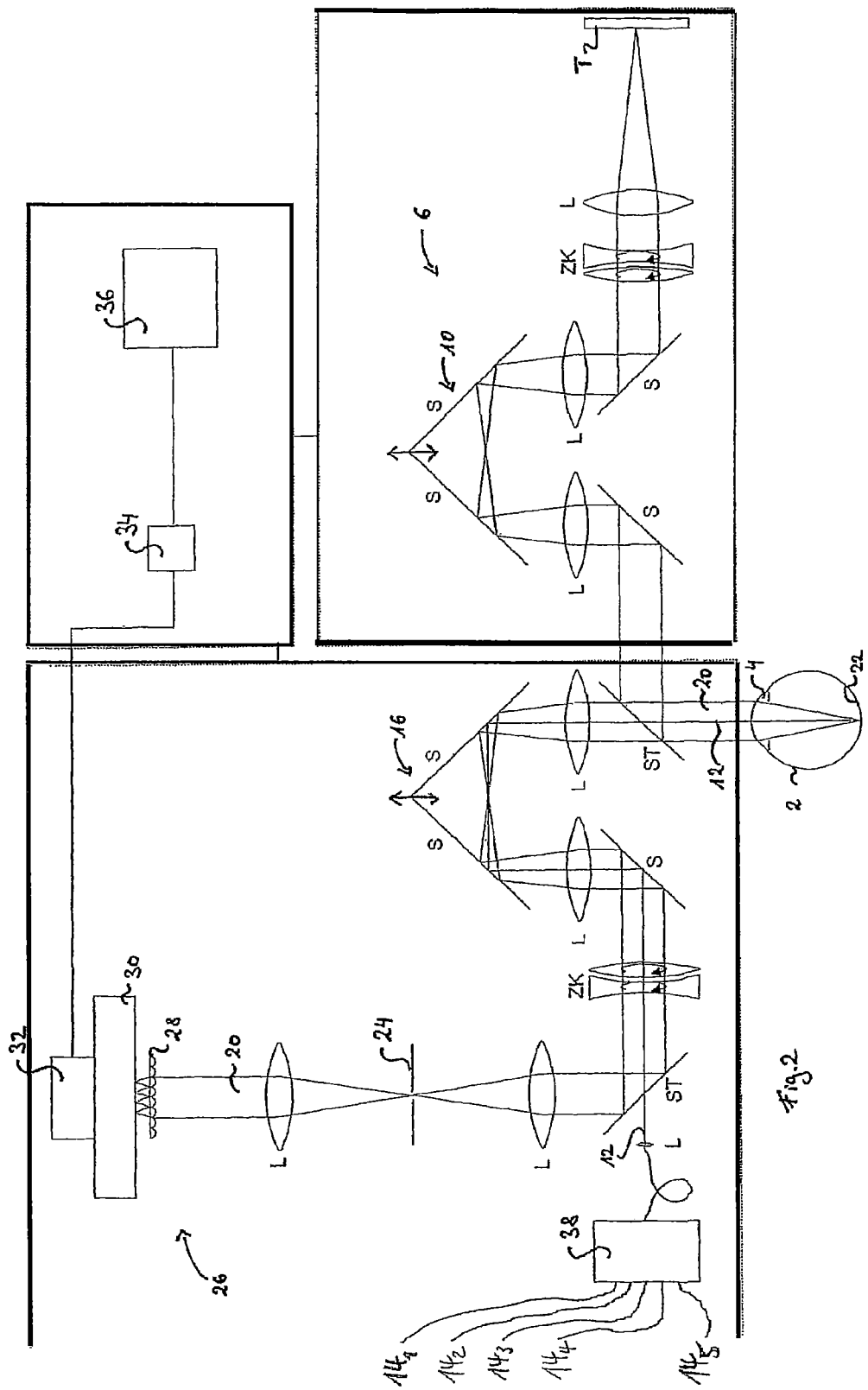
FIG. 2 shows a schematic illustration of a preferred embodiment of the device according to the invention for detecting wave fronts for various wavelengths under a static visual condition.

In FIGS. 1 to 3 lenses L, mirrors S, beam splitters ST and cylindrical compensators ZK are indicated by said reference symbols without further differentiations.

The embodiment schematically illustrated in FIG. 1 serves to detect wave fronts of an eye 2 and in particular of a lens 4 of the eye 2. This embodiment serves in particular to measure wave fronts under dynamic visual conditions for the eye 2 in the form of dynamic accommodation processes.

In order to effect dynamic accommodations of the eye 2 or the lens 4, a stimulus appearing at different distances is provided. For this purpose, an image of a destination or target T, observable as a stimulus, is provided via a stimulus-generating device, in the form of a Badal optometer, designated as a whole by 6. The image of the target T is provided for the eye via lenses L, a cylindrical compensator ZK, mirrors S and a beam splitter ST. In order to make the stimulus or the image of the target T appear at distances which are different to the eye, the stimulus-generating device 6 comprises a mirror or prism arrangement 10, which is movable in the direction of arrow 8.

For measuring, test radiation 12, in this case in the form of laser radiation from a laser 14, is used. The laser 14 may be, for example, a laser, a laser diode or a superluminescent diode (SLD) and emit test radiation 12 which has a wavelength in the range of visible light into the infrared range.

The test radiation is fed to the eye via lenses L, a cylindrical compensator ZK and mirrors S. This arrangement of optical components comprises a mirror or prism arrangement 16, which is movable in the direction of arrow 18. Movements of arrangements 10 and 16 generally take place as a function of one another, in order on the one hand to allow the image of the target T to appear at different distances and on the other hand to take into account the resulting effects for the test radiation and/or the eye in respect of the test radiation.

Test radiation 20, which results after interaction of the test radiation 12 with the eye 2 (in particular interactions based on penetrations of the lens 4 and reflection on the retina 22 of the eye 2), is guided via lenses L, mirrors S, a cylindrical compensator ZK and an aperture 24 to a sensor device designated as a whole by 26. The sensor device 26 serves to detect wave fronts of the test radiation 20.

The sensor device 26 comprises a lens arrangement 28, for example in the form of a microlens array. The lens arrangement 28 may, for example, have lenses with a diameter of 650 μm and a focal length of 30 mm.

Connected downstream of the lens arrangement 28 is an amplifying device 30. The amplifying device 30, for example in the form of an image amplifier, amplifies the test radiation 20, after imaging by the lens arrangement 28, on to appropriate areas of the amplifying device 30.

Use of the amplifying device 30 enables a radiation, the radiant power of which for the eye 2 does not exceed maximum limit values, to be used as test radiation 12. This leads in general to test radiation 12 of relatively low radiant power. After interaction of the test radiation 12 with the eye 2 a test radiation 20 of even lower radiant power results. Normally, this problem is solved in that on the one hand as long exposure times as possible and on the other hand sensors with as much light sensitivity as possible are used. Long exposure times do not allow dynamic visual processes to be analysed. Light sensitive sensors provide only low recording frequencies. By contrast the amplifying device 30 enables on the one hand the radiant power limit values permissible for the eye 2 not to be exceeded and on the other hand faster sensors, which have low light-sensitivity, to be used for detecting wave fronts. The amplifying device 30 serves in particular to provide a sensor 32 with amplified radiation resulting from the test radiation 20, so an adequate signal-to-noise ratio for signal evaluations is achieved.

The sensor 32 is preferably a CMOS sensor with image rates of up to 500 images per second or more.

In particular it is provided that the sensor 32 enables measurements with a frequency of more than 100 Hertz. CMOS sensors are particularly suitable for this owing to their high image rates.

The sensor 32 emits signals corresponding to detected test radiation, which are forwarded to an evaluation device 34. A digital signal processor, for example, may be used as evaluation device 34.

In particular it is provided that the lens arrangement 28 and the sensor 32 represent a Hartmann Shack sensor. The lens arrangement 28 images a dot pattern on to the sensor 32, containing information about wave fronts of the test radiation.

A control device 36 is provided to control the device of FIG. 1. The control device 36 may comprise a personal computer, a microprocessor and the like. The control device 36 controls in particular the operation of the entire device of FIG. 1, including the stimulus-generating device 6 and the sensor device 26.

The schematic illustration in FIG. 2 shows an embodiment which differs from the embodiment according to FIG. 1 as explained below. Components used in both embodiments are indicated by the same reference symbols.

The mobility of the mirror or prism arrangements 10 and 16, also provided in the embodiment of FIG. 2, can be used in the measurements described below, in particular also in static measurements, for pre-compensation of defective vision.

The embodiment of FIG. 2 uses several radiation sources $14_1$-$14_n$ of different, discrete wavelengths to generate the test radiation 12. In FIG. 2 five such radiation sources 14 are illustrated as examples. The radiation sources 14 may, for example, emit radiation in a wavelength range across the entire visible range into the infrared range. The radiation sources 14 may, for example, be lasers, laser diodes and/or SLDs.

Radiation emitted by the radiation sources 14 is transmitted to a switching device 38. The transmission of radiation from the radiation sources 14 to the switching device 38 may take place via fibre-optic conductors, for example.

The switching device 38, for example in the form of a so-called fibre switch, is operated at a switching frequency, in order to emit radiation from the radiation sources 14 at different times and/or at different time intervals and/or for different periods of time as test radiation 12. The order in which radiation from the radiation sources 14 is emitted as test radiation 12 may start, for example, at the smallest (largest) wavelength and progress to the largest (smallest) wavelength, in order then to start again with the smallest (largest) wavelength. It is also possible for the order in which radiation from the radiation sources 14 is emitted as test radiation 12 to be performed in any, chaotic order.

A possible application of the device of FIG. 2 is detection of the chromatic aberration of the eye 2 or the lens 4. For this purpose the eye 2 may be provided with a stimulus, observable as stationary, by the stimulus-generating device 6. In this case the eye 2 is fed with radiations from the radiation sources 14 via the switching device 38 as test radiation 12. The switching device 38 is operated at a switching frequency which is high enough to be able to assume a static state of the eye 2 and in particular of the lens 4. Even if the stimulus-generating device 6 provides a stimulus which appears to be stationary, when a stimulus of this kind is fixed on, the eye is subjected to certain changes which are to a slight extent dynamic, such as, for example, microsaccades. In order to rule out the influence of such changes, the switching device 38 is operated at an appropriately high switching frequency. The switching frequency may amount to 100 Hertz, for example.

After interaction with the eye 2 or the lens 4, as described above with reference to FIG. 1, test radiation 20 is fed to the sensor device 26. Here the test radiation 20 comprises radiations of different wavelengths, namely wavelengths of the radiation sources 14. In order to detect interactions of the test radiation 12 for the different wavelengths of the radiation sources 14 in each case, the sensor device 26 and in particular the sensor 32 are operated during measuring of wave fronts at a scanning frequency (corresponding to the measurement of a wave front), which is at least equal in size to the switching frequency of the switching device 38.

On the basis of the choice of switching frequency of the switching device 38, wave fronts of the test radiation 20, detected by the sensor device 26, indicate the chromatic aberration of the eye 2 or the lens 4 for the different wavelengths.

If the sensor device 26 is operated at a sufficiently high scanning frequency, it is possible to use the device of FIG. 2 both for detecting accommodation-dependent characteristics of the eye 2 and for measuring its chromatic aberration. For an application of this kind it is provided to operate the stimulus-generating device 6 in such a way that dynamic accommodation processes are effected by stimuli appearing at different intervals. In order at the same time to determine characteristics of the eye 2 dependent on wavelengths, the switching device 38 is operated at a switching frequency of such a size that it is possible to assume a static state of the eye for at least one accommodation state, advantageously for several or each accommodation state, in respect of the different wavelengths.

In order to detect the information then present in the test radiation 20, the sensor device 26 and in particular the sensor 32 should be operated at a scanning frequency corresponding to a whole-number which is many times the product of the frequencies at which the stimulus-generating device 6 and the switching device 38 are operated.

The embodiment schematically illustrated in FIG. 3 is used for measuring the dispersion of a lens for an eye. The lens 4 may be, for example, a contact lens or an intra-ocular lens. Comparably to the embodiment of FIG. 2, the embodiment of FIG. 3 comprises radiation sources $14_1$-$14_n$, which emit radiation of different wavelengths. The explanations given in this connection with reference to FIG. 2 apply correspondingly here. This also applies to the switching device 38 containing radiation from the radiation sources 14. Test radiation 12 emitted by the switching device 38 is fed to the lens 4 directly or via optics arranged between the switching device 38 and the lens 4, which in FIG. 3 comprise an exit lens L and a lens $L_s$ for beam expansion for representational purposes only. Test radiation 20, resulting from interaction of the test radiation 12 with the lens 4, is fed to a sensor device 26 via optics comprising, as an example, lenses L and a cylindrical compensator ZK (in particular for pre-compensation) and an aperture B1 with a lens L connected downstream.

The sensor device 26 is substantially comparable to the sensor devices 26 of FIGS. 1 and 2. This applies in particular to the scanning rates at which the sensor device 26 is operated.

With the embodiment of FIG. 3 it is possible to determine the dispersion, i.e. the wavelength-dependent refraction of light through the lens 4. In the case of contact lenses and intraocular lenses the sensor device 26 is also operated at a scanning frequency of a level as explained above, which has the advantage that examining wavelength-dependent properties of lenses for eyes, for example in the context of industrial manufacture of contact lenses, can be done particularly quickly. With the device of FIG. 3 it is further possible to improve quality control.

In the above description of the embodiments of FIGS. 1 and 2 it is assumed that the lens 4 of the eye 2 is its own lens. However, it is also possible to use the embodiments of FIGS. 1 and 2 for measuring on an eye which additionally has a contact lens or in which an intra-ocular lens is used. It is also possible to use the devices from FIGS. 1 and 2 for measuring on an eye which is subjected to refractive surgical treatment.

What is claimed is:

1. A device for measuring wave fronts generated by a lens for an eye, comprising:
    a radiation source comprising at least one source for laser radiation emitted at a fixed preset wavelength, the radiation source configured to emit test radiation to be directed at the lens; and
    a sensor device configured to:
        detect wave fronts of the test radiation after interaction with the lens, changes in the wave fronts occurring in the test radiation at a wave front changing frequency; and
        detect the test radiation at a scanning frequency that is at least equal to the wave front changing frequency, wherein the scanning frequency is at least 70 Hertz.

2. The device of claim 1, further comprising a stimulus-generating device configured to generate stimulus effecting dynamic changes to the lens.

3. The device of claim 2, wherein the scanning frequency is at least equal in size to the frequency of the dynamic changes to be effected to the lens.

4. The device of claim 2, wherein the stimulus-generating device is a Badal optometer.

5. The device of claim 1, wherein the sensor device is an optical sensor.

6. The device of claim 5, wherein the optical sensor is a CMOS sensor.

7. The device of claim 1, wherein the scanning frequency of the sensor device is 100 Hertz or more.

8. The device of claim 1, further comprising an amplifying device configured to amplify the test radiation before detection by the sensor device.

9. The device of claim 1, wherein the fixed preset wavelength of the laser radiation is between 400 nm and 1000 nm.

10. The device of claim 1, wherein the radiation source includes at least one of a laser, a laser diode, and a superluminescent diode.

11. The device of claim 1, wherein the radiation source comprises multiple radiation sources configured to emit laser radiation at a fixed preset wavelength, a first of the radiation sources configured to emit laser radiation at a first fixed preset wavelength and a second of the radiation sources configured to emit laser radiation at a second fixed preset wavelength different than the first fixed preset wavelength.

12. The device of claim 11, further comprising a switching device coupled to the first and second radiation sources and configured to control emission of the laser radiation to the lens from the first and second radiation sources at a switching frequency.

13. The device of claim 12, wherein the switching device is at least one of a fiber switch and a fiber-optic coupler.

14. The device of claim 12, wherein the scanning frequency is at least equal in size to the switching frequency.

15. The device of claim 14, wherein the switching frequency is approximately 100 Hertz.

* * * * *